(12) United States Patent
Yamaguchi et al.

(10) Patent No.: US 7,684,937 B2
(45) Date of Patent: Mar. 23, 2010

(54) EVALUATION METHOD OF FINE PATTERN FEATURE, ITS EQUIPMENT, AND METHOD OF SEMICONDUCTOR DEVICE FABRICATION

(75) Inventors: Atsuko Yamaguchi, Kudaira (JP); Hiroshi Fukuda, Tokyo (JP); Hiroki Kawada, Tuchiura (JP); Tatsuya Maeda, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 52 days.

(21) Appl. No.: 12/078,840

(22) Filed: Apr. 7, 2008

(65) Prior Publication Data
US 2008/0215274 A1 Sep. 4, 2008

Related U.S. Application Data

(63) Continuation of application No. 11/185,852, filed on Jul. 21, 2005, now Pat. No. 7,366,620.

(30) Foreign Application Priority Data
Jul. 30, 2004 (JP) ............................. 2004-222737

(51) Int. Cl.
*G01B 5/28* (2006.01)
(52) U.S. Cl. .......................................... 702/40; 702/82
(58) Field of Classification Search ................... 702/40, 702/82
See application file for complete search history.

(56) References Cited

U.S. PATENT DOCUMENTS 6,480,807 B1 * 11/2002 Miyano ...................... 702/159

| | | | |
|---|---|---|---|
| 2003/0021463 A1 | 1/2003 | Yamaguchi et al. | |
| 2003/0142399 A1 | 7/2003 | Schoeppe | |
| 2004/0195507 A1 * | 10/2004 | Yamaguchi et al. | 250/310 |
| 2009/0114816 A1 * | 5/2009 | Tam et al. | 250/307 |

FOREIGN PATENT DOCUMENTS

JP 2002-243428 2/2001

OTHER PUBLICATIONS

Oldiges, Phil, "Modeling Line Edge Roughness Effects in sub 100 Nanometer Gate Length Devices", IEEE, 2000, pp. 131-134.

(Continued)

*Primary Examiner*—Bryan Bui
*Assistant Examiner*—Jonathan Teixeira Moffat
(74) *Attorney, Agent, or Firm*—Stites & Harbison PLLC; Juan Carlos A. Marquez, Esq.

(57) ABSTRACT

Equipment extracts components of spatial frequency that need to be evaluated in manufacturing a device or in analyzing a material or process out of edge roughness on fine line patterns and displays them as indexes. The equipment acquires data of edge roughness over a sufficiently long area, integrates components corresponding to a spatial frequency region being set on a power spectrum by the operator, and displays them on a length measuring SEM. Alternatively, the equipment divides the edge roughness data of the sufficiently long area, computes long-period roughness and short-period roughness that correspond to an arbitrary inspection area by performing statistical processing and fitting based on theoretical calculation, and displays them on the length measuring SEM.

9 Claims, 13 Drawing Sheets

OTHER PUBLICATIONS

Young, K.K., "A 0.13 µm CMOS Technology with 193 nm Lithography and Cu/Low-k for High Performance Applications", IEEE, 2000, pp. 1-4.

Diaz, Carlos H., "An Experimentally Validated Analytical Model for Gate Line-Edge Roughness (LER) Effects on Technology Scaling", IEEE electron Device Letters, vol. 22, No. 6, Jun. 2001, pp. 287-289.

Xiong, Shiying, "Study of Gate Line Edge Roughness Effects in 50 nm Bulk MOSFET Devices", Proceedings of SPIE vol. 4689, 2002, pp. 733-741.

Linton, T., "Determination of the Line Edge Roughness Specification for 34 nm Devices", IEEE 2000, pp. 1-4.

Croon, J.A., "Line Edge Roughness: Characterization, Modeling and Impact on Device Behavior", IEEE, 2002, pp. 1-4.

Yamaguchi, A., "Characterization of line-edge roughness in resist patterns and estimations of its effect on device performance", Metrology, Inspection, and Process Control for Microlithography XVII, Proceedings of SPIE vol. 5038, 2003, 689-698.

* cited by examiner

EVALUATION METHOD OF FINE PATTERN FEATURE, ITS EQUIPMENT, AND METHOD OF SEMICONDUCTOR DEVICE FABRICATION

CROSS REFERENCE TO RELATED APPLICATIONS

This application is a Continuation of U.S. patent application Ser. No. 11/185,852, filed Jul. 21, 2005 now U.S. Pat. No. 7,366,620. Priority is claimed based on U.S. patent application Ser. No. 11/185,852, filed Jul. 21, 2005, which claims priority from Japanese application JP 2004-22737 filed on Jul. 30, 2004, all of which is hereby incorporated by reference into this application.

FIELD OF THE INVENTION

The present invention relates to an evaluation method of fine pattern feature by detailed feature metrology by means of non-destructive observation with a scanning electron microscope (SEM) and image processing or by dimensional measurement, its inspection equipment, and a method of semiconductor device manufacture.

BACKGROUND OF THE INVENTION

Recently, with improvement in fine pattern processing technologies in semiconductor and other industries, small deviations from design values of the pattern become problems. Especially, degradation in a two-dimensional form and dimensional variation that are noticeable even by top-down observation cause large influence in device performance. Then, there has arisen a need to measure and evaluate edge roughness and amount of CD variation (CD uniformity across a wafer top surface, CD variation among wafers, etc.) more correctly. For example, edge roughness occurred in the gate of a transistor causes, first, a local short channel effect. Therefore, even if the average gate length in the transistor has such a value as a design specifies, transistor performance gets worse than a design value. Second, the average gate length in the transistor itself deviates from the design value.

Recently, influence of edge roughness described above, especially edge roughness on a line pattern (line-edge roughness), on transistor performance has started to be discussed actively, as described in, for example, Non-patent literatures 1 to 7. As a result, a problem of measurement of line-edge roughness in addition to the conventional dimensional measurement has arisen also in measurement equipment. Generally, a difference between a maximum value and minimum value obtained by statistically processing roughness data (sequence data) that are obtained by measuring edge points of a line pattern or line widths at constant intervals, three times the standard deviation of its distribution, or the like is used as an index of line-edge roughness. However, determination using one kind of index out of these indexes has two problems. First, this determination cannot compare data of different sampling conditions. This is because an index value depends largely on sampling conditions of the data (a dimension of measurement area used to compute a degree of roughness and a sampling interval at which edge points are extracted) as described in Non-patent document 7. For example, in the case where two kinds of patterns A and B are measured with respective different observation magnifications, it is very difficult to equalize a detection interval of edge-points used to calculate line-edge roughness and a measurement area for two kinds of images, because the length and resolution for one pixel are different.

For this reason, regarding the degree of roughness, it is often the case that discussion is given up and the roughness is measured again. Such a problem is likely to occur in a research and development phase. Second, a spatial period of roughness cannot be expressed with one kind of index. For example, in the case of the line-edge roughness on the gate described at the beginning, the roughness that produces a local short channel effect described as the first example is of a comparatively short period. On the other hand, this roughness that produces a shift in the average gate length described in the second example is of a long period. In a process of making transistors of short gate widths, roughness of a long period becomes comparatively large. Therefore, although the performance of individual transistors does not degrade, performance variation as a whole becomes large. On the other hand, in a manufacturing process of transistors of long gate widths, performance variation is small, but a short channel effect is easy to occur for every transistor.

In order to realize high productivity in a semiconductor mass-production system, it is necessary to perform evaluation suitable for properties of a product and its transistor structure. For that purpose, an index containing characteristics of spatial frequency becomes necessary besides only measuring a degree of line-edge roughness always under constant measurement conditions.

What is necessary to indicate characteristics of spatial periods of line-edge roughness is to Fourier transform roughness data obtained by measuring edge points of a line pattern or line widths at constant intervals and display its Fourier spectrum (amplitude spectrum or power spectrum). This is for solving the second problem described above, but at the same time can solve the first problem. By comparing the magnitude of each frequency component of the Fourier spectrum, the magnitude relation of roughness can be determined regardless of measurement conditions of the roughness data.

In research and development, these techniques are employed. As described in Non-patent literatures 7 to 9, there are examples of actual reports. However, it is difficult to grasp instantaneously characteristics of the line-edge roughness related to the frequency distribution visually from these spectra on which noises have a large influence. It takes a time to compare and examine Fourier spectra having a lot of noises visually and involves a possibility that different results are obtained depending on a viewer. So, an index that simply represents the characteristics of a frequency distribution becomes necessary. Especially in an inspection process in volume production, the need is larger.

Moreover, the conventional CD measurement is not predicated the existence of line-edge roughness. For example, in the presence of line-edge roughness, CD may vary depending on which position is measured on the line. Because of this, measured values of CD uniformity across a wafer plane and amount of variation among wafers depend on line-edge roughness occurring at random, and consequently it becomes impossible to measure CD variation resulting from variation in anneal temperature and variation in an underlayer thickness. For the method of CD measurement, a countermeasure is becoming necessary.

Note that a term, line-edge roughness is a term indicating a variation in edge positions of a line pattern. However, it is often the case that this term is used for both a variation in edge positions and a variation in line widths along the line. Hereafter, as a term especially for a variation in edge positions, an expression of the line-edge roughness in the narrow sense will be used. Moreover, an expression of line width roughness will be used for a variation in line width along the line.

[Non-patent document 1]Digest of SISPAD 2000 (2000), pp. 131-134

[Non-patent document 2]IEDM Technical Digest 2000 (2000), pp. 563-567

[Non-patent document 3]IEEE Electron Device Letters, Vol. 22 (2001), pp. 287-289

[Non-patent document 4]Proc. SPIE 4689 (2002), pp. 733-741

[Non-patent document 5]IEDM Technical Digest 2002 (2002), pp. 303-306

[Non-patent document 6]IEDM Technical Digest 2002 (2002), pp. 307-310

[Non-patent document 7]Proc. SPIE 5038 (2003), pp. 689-696

SUMMARY OF THE INVENTION

Against the background described above, there is required an index that sums up characteristics of a Fourier spectrum of line-edge roughness. Moreover, in order to measure correctly CD variation factors other than line-edge roughness, a measurement method of CD that suffers no effect from line-edge roughness is necessary.

The problem that this invention intends to solve is to provide a method of calculating characteristics of a frequency distribution of line-edge roughness and characteristics of a fine line pattern that is represented by a line width exclusive of line-edge roughness, and equipment therefore.

The simplest embodiment according to this invention is a method of extracting and outputting components belonging to a specific frequency band. A power spectrum is a square of absolute value of Fourier series that is obtained by Fourier transforming results obtained by measuring positions of points that constitute a boundary of a fine pattern at constant intervals along a line serving as a reference, namely roughness data of pattern edges or roughness data of pattern dimensions. The power spectrum is written as P(f). Here, f is the spatial frequency, expressed in units of $\mu m^{-1}$. At this time, a following relationship exists between the statistical standard deviation σ of an original roughness data and P(f).

$$\sigma^2 = \sum_f P(f) \qquad \text{[Numerical expression 1]}$$

Next, the operator sets up a range of f to which attention is paid among this integration region in the right side. When the operator specifies the integration region of f as from a $\mu m^{-1}$ to b $\mu m^{-1}$, the component $\sigma_c$ of this region is calculated by the following Numerical expression.

$$\sigma_c^2 = \sum_{a \leq f \leq b} P(f) \qquad \text{[Numerical expression 2]}$$

That is, a sum of all P(f) that satisfy $a \leq f \leq b$ becomes $\sigma_c^2$.

When the operator wishes to calculate this amount for a high volume of samples, observation equipment for inspection or a computer that has been set to enable the operator to call observation results is set capable of executing the above-mentioned procedure. It is recommendable to set the values of a and b in advance so that entry of these values at each inspection is eliminated and configure the computer to be able to recall these values automatically and execute calculation.

As indexes of these values, $\sigma_c^2$, $\sigma_c$, $2\sigma_c$, $3\sigma_c$, and $6\sigma_c$ are suitable. Among them, $\sigma_c^2$ can be found directly by the above-mentioned calculation. What is necessary to obtain other indexes is just to multiply a square root of $\sigma_c^2$ by 1, 2, 3, and 6, respectively. Incidentally, the operator is requested to set in advance as to which index is used. One set of roughness data and a value of index obtained from the values of a and b being set are outputted on observation equipment for inspection or a computer. Moreover, they can be recorded automatically as an electronic file.

If such a method is used, it is possible to quickly obtain the components of roughness in an arbitrary frequency region band being set up in advance without the necessity of determination of the operator and save the results so that the results can be checked later.

For patterns to be used, various patterns may be used. Especially, line patterns are recommendable. This is because line patterns allow an arbitrarily interval at which the data is acquired. For example, in the case where the diameter of dense hole patterns is used as the roughness data, the interval between the data must be set equal to a spatial period of the pattern.

As the roughness data to be used, data obtained from an area over a length of 2 µm or more is preferable. This is because that such data enables analysis of roughness components having a sufficiently long period. A ground of this value is shown in Non-patent document 7. According to this literature, although the magnitude of line-edge roughness depends strongly on the length L in the line direction of an area where metrology is performed (in this invention, this corresponds to the length of the roughness data), the dependency become extremely small if L increases to 2 µm or more. This indicates that when analyzing the roughness, all that should be done is to measure an area that is as large as about 2 µm and conversely that if an area as large as 2 µm is not measured, behaviors of long period components of roughness cannot be grasped. Moreover, for an interval when obtaining the roughness data, a value smaller than 10 nm is preferable. This is because components of sufficiently short periods can be analyzed. According to Non-patent document 7, it is necessary to extract a feature of an edge at intervals of 10 to 20 nm in order to calculate the magnitude of roughness with an error of 5% or less when observing the roughness in an area of L=2 µm. Therefore, a sampling interval of 10 nm or less is recommendable here.

In the method described above, it is possible to define a value of index whose integration region is specified to be from 0.5 $\mu m^{-1}$ to a certain fixed value as a long period component or a low frequency component. Moreover, it is possible to define a value of index whose integration region is specified to be from a certain fixed value to 100 $\mu m^{-1}$ as a short period component or a high frequency component. It is preferable to use a value from unity to 10 inclusive as an upper limit of the integration region for calculation of the long period component and a lower limit of the integration region for calculation of the short period component both described here. This is because in many cases, a spatial frequency distribution of line-edge roughness (Fourier amplitude spectrum) consists of a region where the amplitude is proportional to an inverse of the spatial frequency and a region where the amplitude is proportional to m-th power of the spatial frequency (a value of m is from zero to 0.3 at the highest), and a frequency ($f_0$) that becomes a boundary of the two regions exists between 1 $\mu m^{-1}$ and 10 $\mu m^{-1}$ (Note that a graph of FIG. 1 has logarithmic spacing on the horizontal and vertical axes). An origin of this phenomenon is unknown, but it is conjectured that an occurrence mechanism of roughness changes in this region as a boundary. Therefore, it is reasonable from the standpoint of roughness analysis that the roughness is divided into two at this boundary and each is expressed in a numerical term. Standardizing the integration region in this way has an effect that setting of a value of the integration region can be simplified. Incidentally, there are other determination methods of integration region. For example, an inverse of a gate width $w_g$ of a transistor to which attention is paid may be used as the upper limit of the integration region for calculation of the long period component or the lower limit of the integration region for calculation of the short period component. This may be called a method that considers an influence to the device rather than a cause of roughness occurrence.

Moreover, in the case where this method is applied specially to line width roughness, if a component of f=0 is extracted simultaneously, a line width exclusive of an effect of fluctuation can be obtained. This value is also equal to the arithmetical mean of all the roughness data.

For an evaluation method of line-width roughness that reflects the frequency distribution, additionally there is a method shown in the following. That is, the method is for computing the short-period roughness component that causes performance degradation of a transistor of a typical size that is made from the line pattern, namely the first roughness described above, and the long-period roughness that causes performance variation, namely the second roughness. (This method is not an evaluation method of line-edge roughness in the narrow sense.) An outline procedure is as follows.

First, roughness data points of line widths $w_1, w_2, \ldots, w_{M'}$ is acquired on a line pattern, as shown in FIG. 2. The length of the observation range in which these data points were obtained in a direction along the line is named as $L_1$. The standard deviation of these M' data points, $w_1, w_2, \ldots, w_{M'}$ is calculated and defined as $\sigma_0$. This value serves as an index of the magnitude of the line width roughness occurred in a transistor area when the transistor of a gate width $L_1$ is made.

A group consisting of consecutive M data points is taken out from this set of roughness data points. The number of groups is set to N. That is, a first group consists of $w_1, w_2, \ldots, w_M$ and a second group consists of $w_{M+1}, w_{M+2}, \ldots, w_{2M}$. Here, N and M satisfy Numerical expression 3.

$$N \cdot M \leq M'$$ [Numerical Expression 3]

The length of the observation area where M data are obtained is named as $L_2$.

Next, the average and the standard deviation of data points are computed for each group. Since this gives N values of standard deviation, the average of these values is calculated and defined as $\sigma_1$. This value serves as an index of the magnitude of the line width roughness occurred in a transistor area when the transistor of a gate width $L_2$ is made. Since the above procedure gives N average line widths, the standard deviation of these values is calculated and defined as $\sigma^2$. This value serves as an index of the variation in the CD value among transistors when a transistor of a gate width $L_2$ is made.

Next, two curves defined as a set of following fitting curves are fitted to three points, P ($L_1, \sigma_0$), Q ($L_2, \sigma_1$), and R ($L_2, \sigma_2$) that were obtained in the above-mentioned procedure.

$$\sigma_i = \alpha \cdot g(L) \ (i=0,1)$$

$$\sigma_2 = \alpha \cdot h(L)$$ [Numerical expression 4]

Here, $\alpha$ is a fitting parameter, and g (L) and h (L) are functions obtained based on theoretical calculation. Examples of these two function forms obtained from theoretical calculation will be described below.

First, absolute values of discrete Fourier coefficients are assumed with a function shown in FIG. 1. Next, phases of the discrete Fourier coefficients are given random numbers. Since by this, the discrete Fourier coefficients are assumed, roughness data points of virtual line width roughness can be prepared by inverse Fourier transforming them. It is difficult to acquire actually actual roughness data points corresponding to an area equal to or more than 10 μm, but in calculation like this, it is possible to lengthen the area length L and shorten the intervals as much as a computer system allows.

The standard deviation of the virtual roughness data points obtained in this way is named as $\sigma_{max}$. Next, an index of line width roughness within a transistor area $\sigma\_intra(L)$ and an index of variation in the CD value among transistors $\sigma\_inter(L)$ when transistors of an arbitrary gate width L are made are calculated from these roughness data points, and g(L) and h(L) are defined as follows.

$$g(L) = \sigma\_intra(L) / \sigma_{max}$$

$$h(L) = \sigma\_inter(L) / \sigma_{max}$$ [Numerical expression 5]

Note that in this case, g (L) and h (L) become functions of parameters m and $f_0$ that are used when assuming the discrete Fourier coefficients. In this case, fitting parameters become $\alpha$, m, and $f_0$. As an example, g(L) and h(L) obtained in the case of m=0.1 are shown in FIG. 3.

Further, it is also possible to obtain more suitable fitting functions g (L) and h (L) by assuming the Fourier amplitude spectrum in other function forms.

Next, an index of short-period roughness $3\sigma\_intra(w_g)$ and an index of long-period roughness $3\sigma\_inter(w_g)$ are computed from the gate width $w_g$ of a transistor that is to be made from an inspection target pattern and the obtained fitting parameters. Here, $3\sigma\_intra(w_g)$ and $3\sigma\_inter(w_g)$ are expressed by the following Numerical expressions.

$$3\sigma\_intra(w_g) = 3\alpha \cdot g(w_g)$$

$$3\sigma\_inter(w_g) = 3\alpha \cdot h(w_g)$$ [Numerical expression 6]

Values of $3\sigma\_intra$ and $3\sigma\_inter$ obtained in this way are directly linked with a distribution of transistor performance. For example, it is possible to evaluate easily the distribution of transistor performance by using the values of $3\sigma\_intra$ and $3\sigma\_inter$ obtained by the above-mentioned concrete procedure as values of the short-period roughness and long-period roughness discussed in Non-patent document 7. Moreover, at this time, observation results of a sufficiently long area are necessary in order to keep reliability of the fitting high. For this purpose, it is appropriate to set the length of an area where original roughness data is acquired to 2 μm or more. Second, in performing statistical processing to calculate the standard variation, an ample number of samples are needed. For this purpose, it is appropriate to set the number of groups N to six or more.

The evaluation method of fine pattern feature and its equipment according to this invention enable a frequency component causing important influence, especially in device performance, among frequency components of line-edge roughness to be extracted and expressed in a numerical term. Since the frequency band of a component affecting the device performance depends on a device structure and final specifications of a product, setting must be altered easily by the equipment operator. This invention allows for the operator to alter setting, and therefore can realize order-made inspection suited to a product, increasing productivity.

DETAILED DESCRIPTION OF THE PREFERRED EMBODIMENTS

First Embodiment

Figure 1:
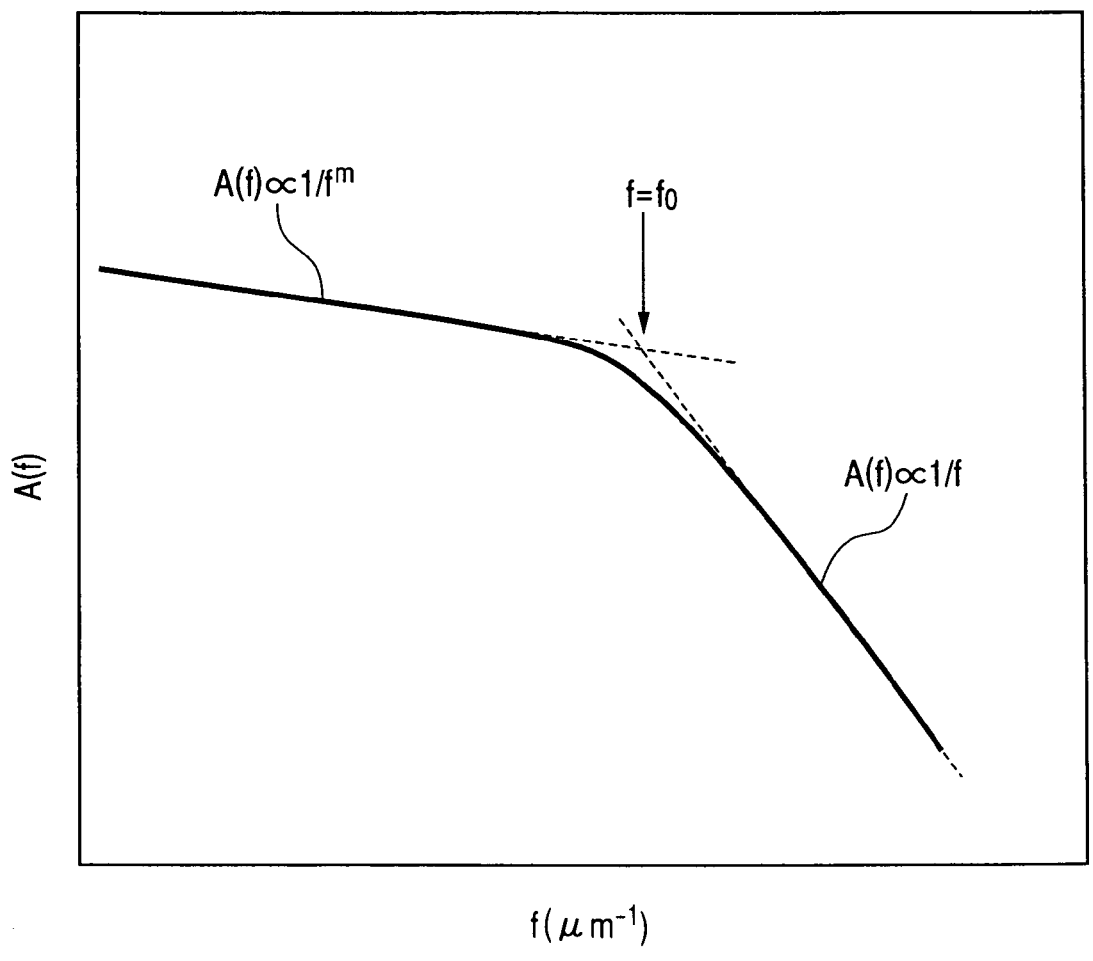
FIG. 1 is a schematic diagram showing a function form of a Fourier amplitude spectrum of general line-edge roughness.
Figure 2:
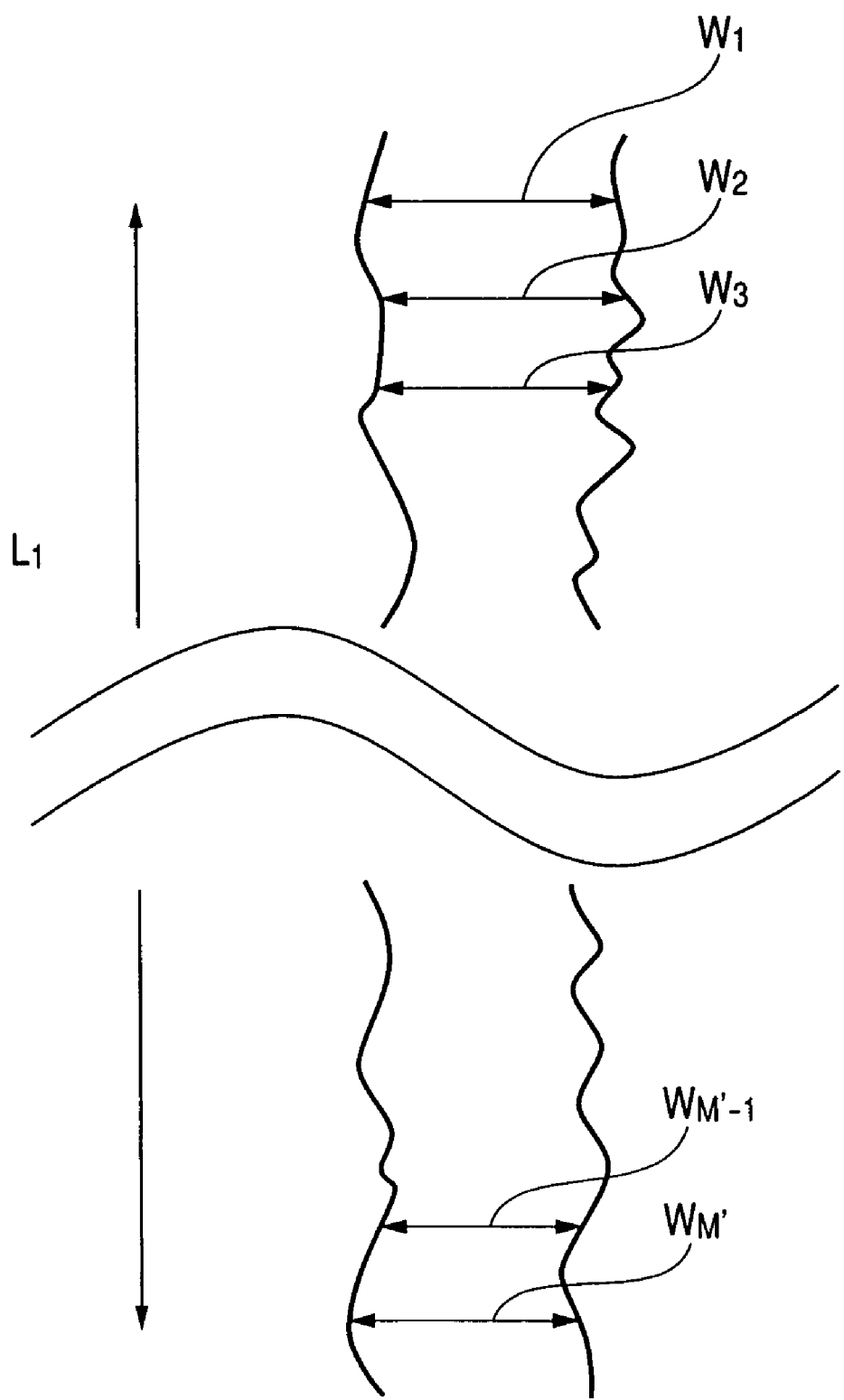
FIG. 2 is a conceptual diagram showing a method of acquiring roughness data of line widths that are analyzed by this invention.
Figure 3:
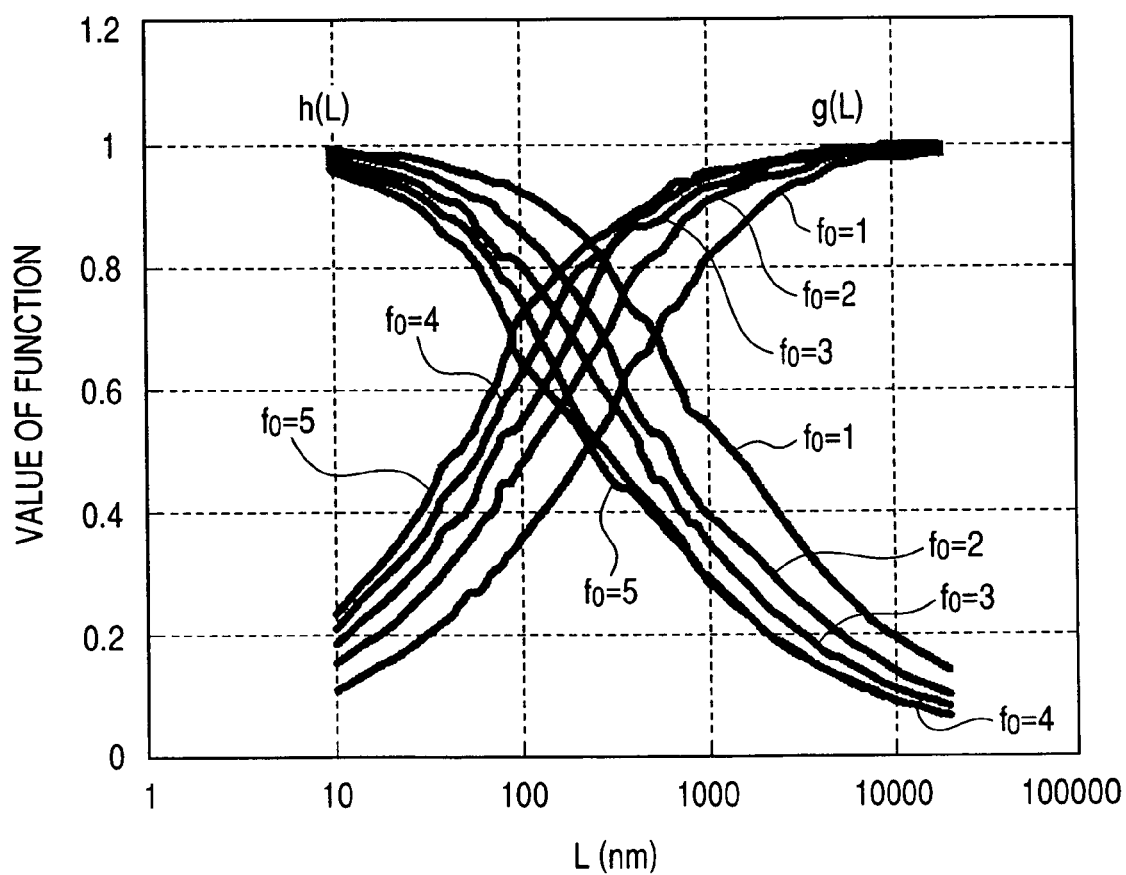
FIG. 3 is an example of a function expressing dependencies of the magnitudes of long-period roughness and short-period roughness on the length of an inspection area.
Figure 4:
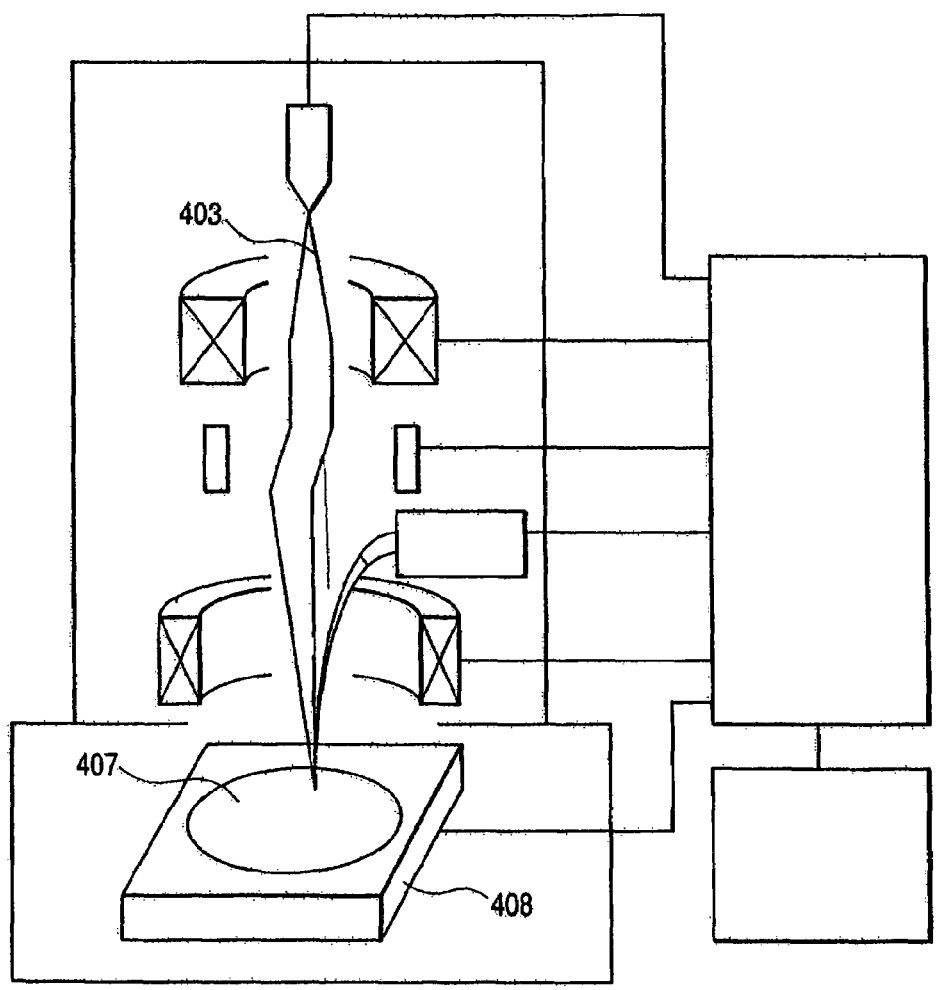
FIG. 4 is a conceptual diagram showing an equipment structure of first, second, and fourth embodiments of this invention.
Figure 5:
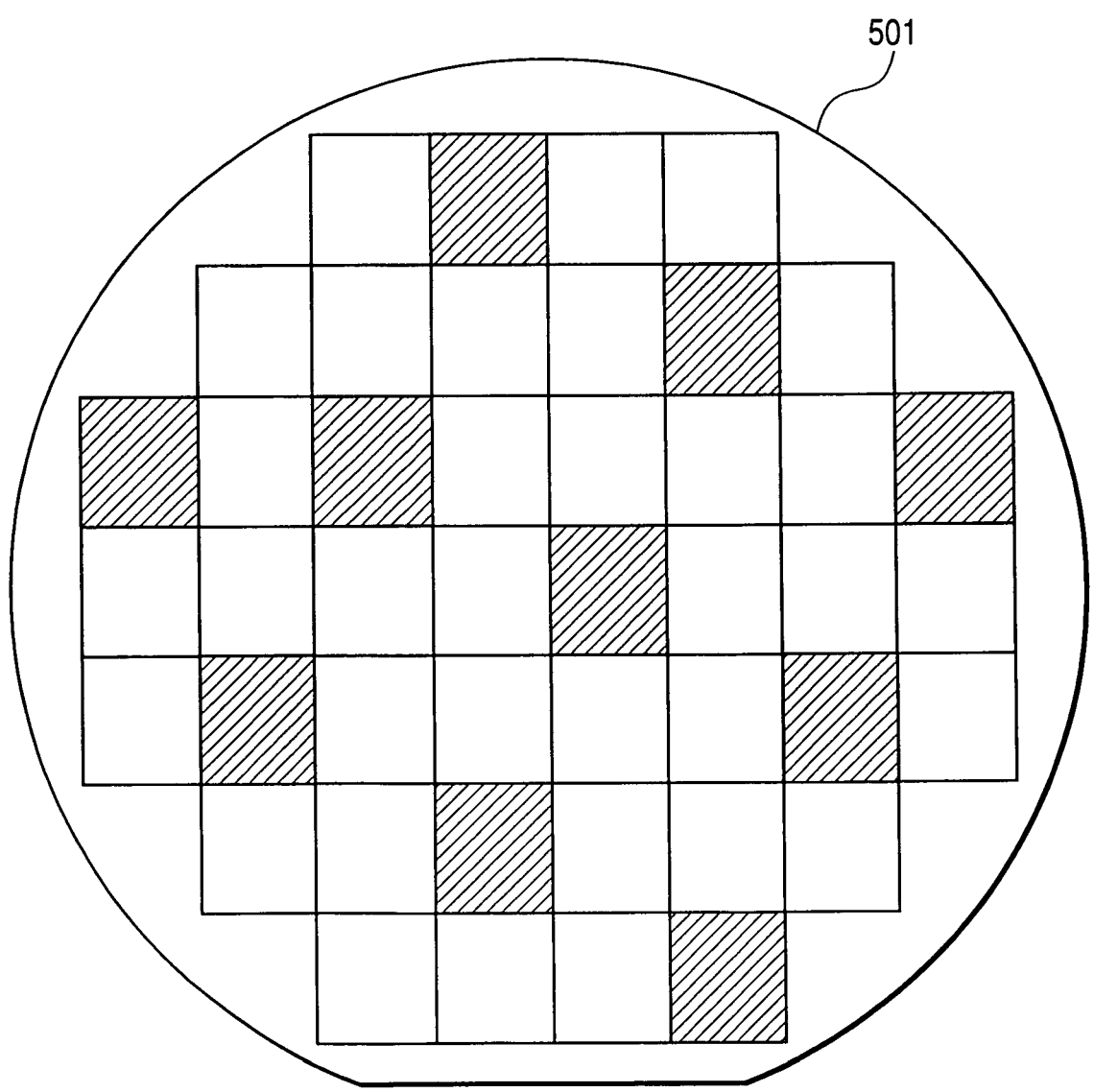
FIG. 5 is a conceptual diagram showing positions of the chips on a wafer that were inspected in the first, second, and fourth embodiments of this invention.
Figure 6:
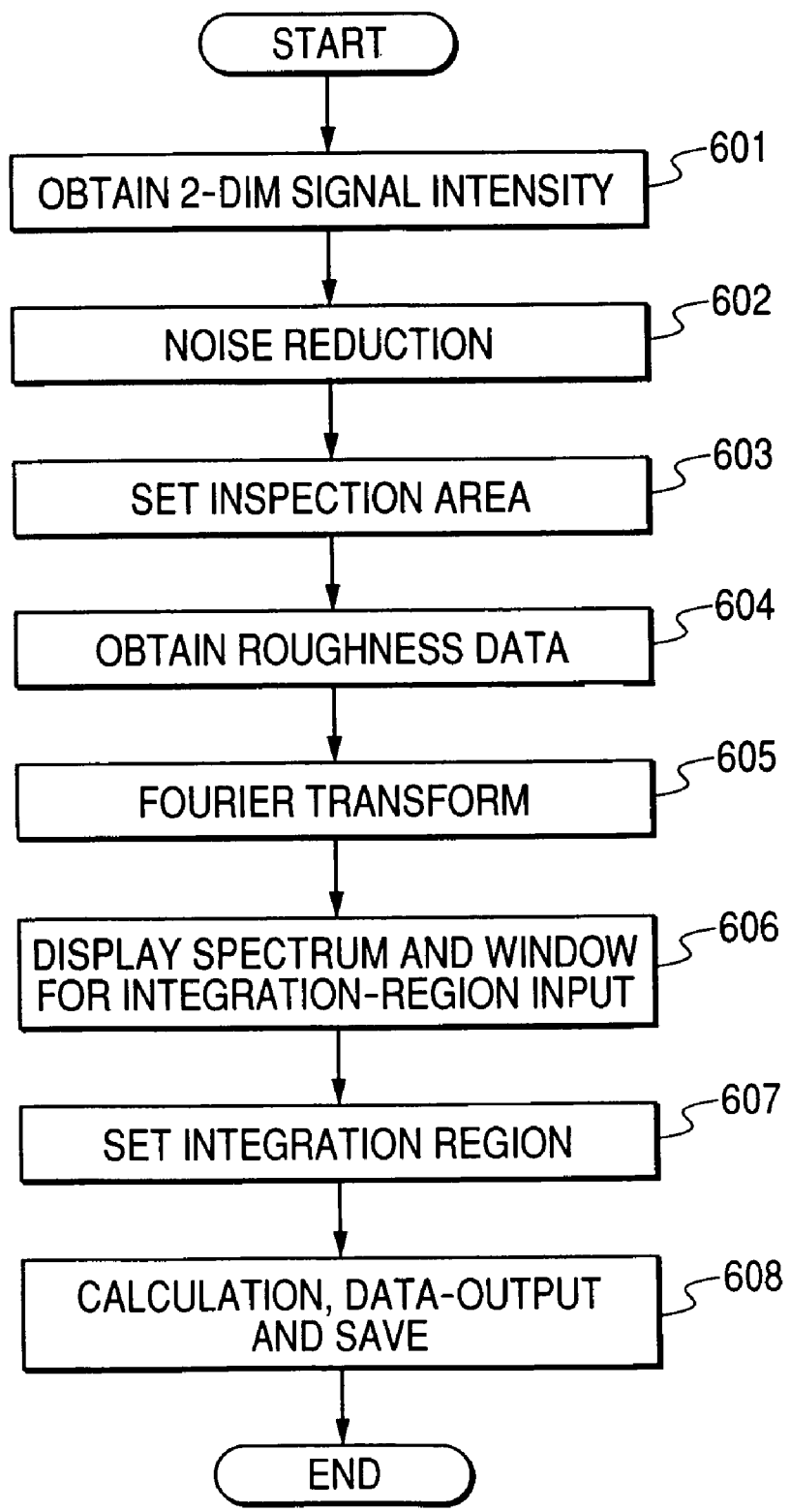
FIG. 6 is a flowchart showing a part of procedure in the first and a third embodiments of this invention.
Figure 7:
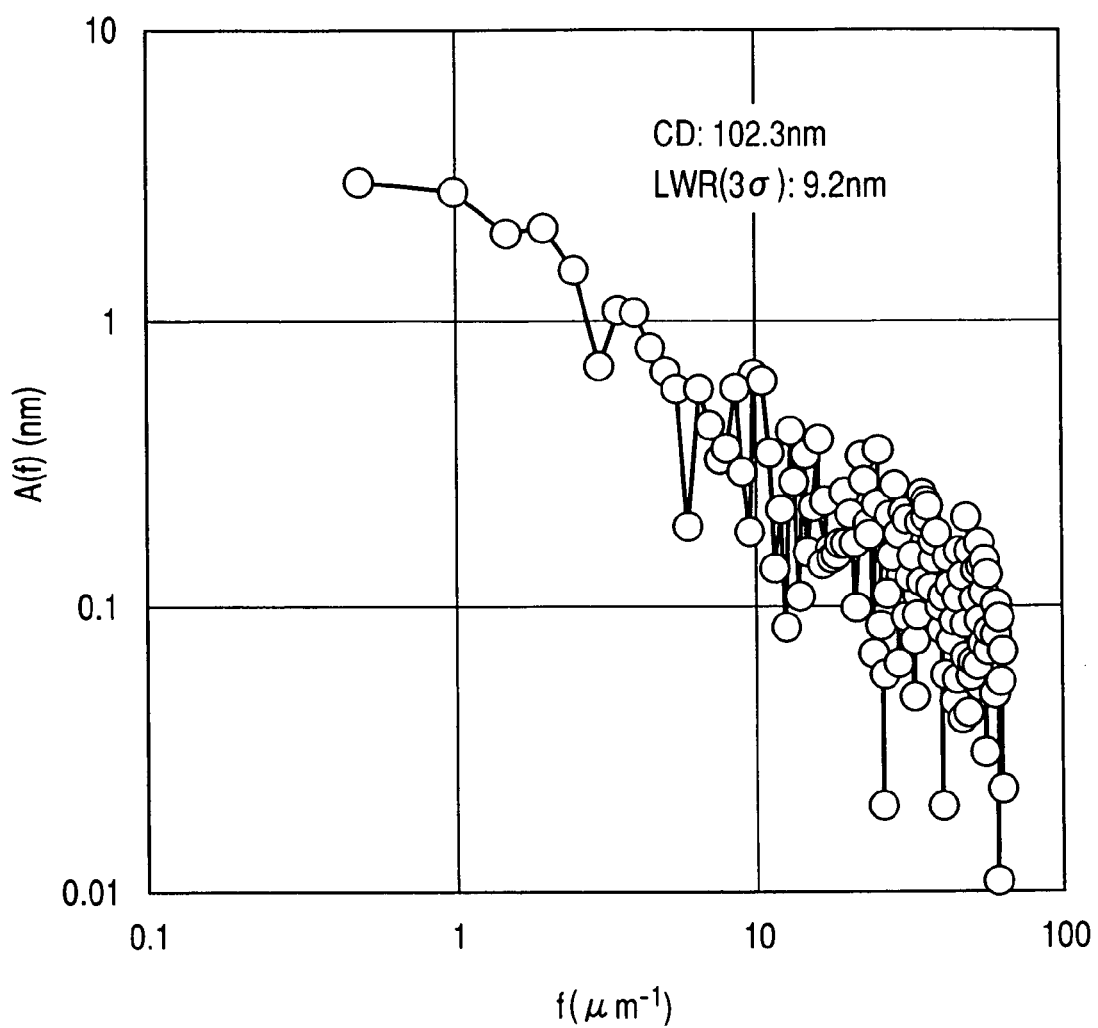
FIG. 7 is a Fourier amplitude spectrum analyzed in the first embodiment of this invention.
Figure 8:
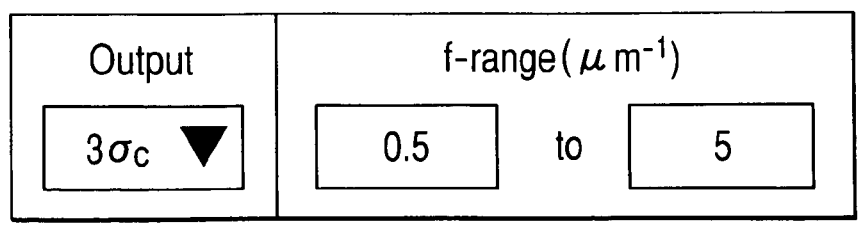
FIG. 8 is a window for integration-region input that appears on a screen of inspection equipment in the first embodiment of this invention.
Figure 9:
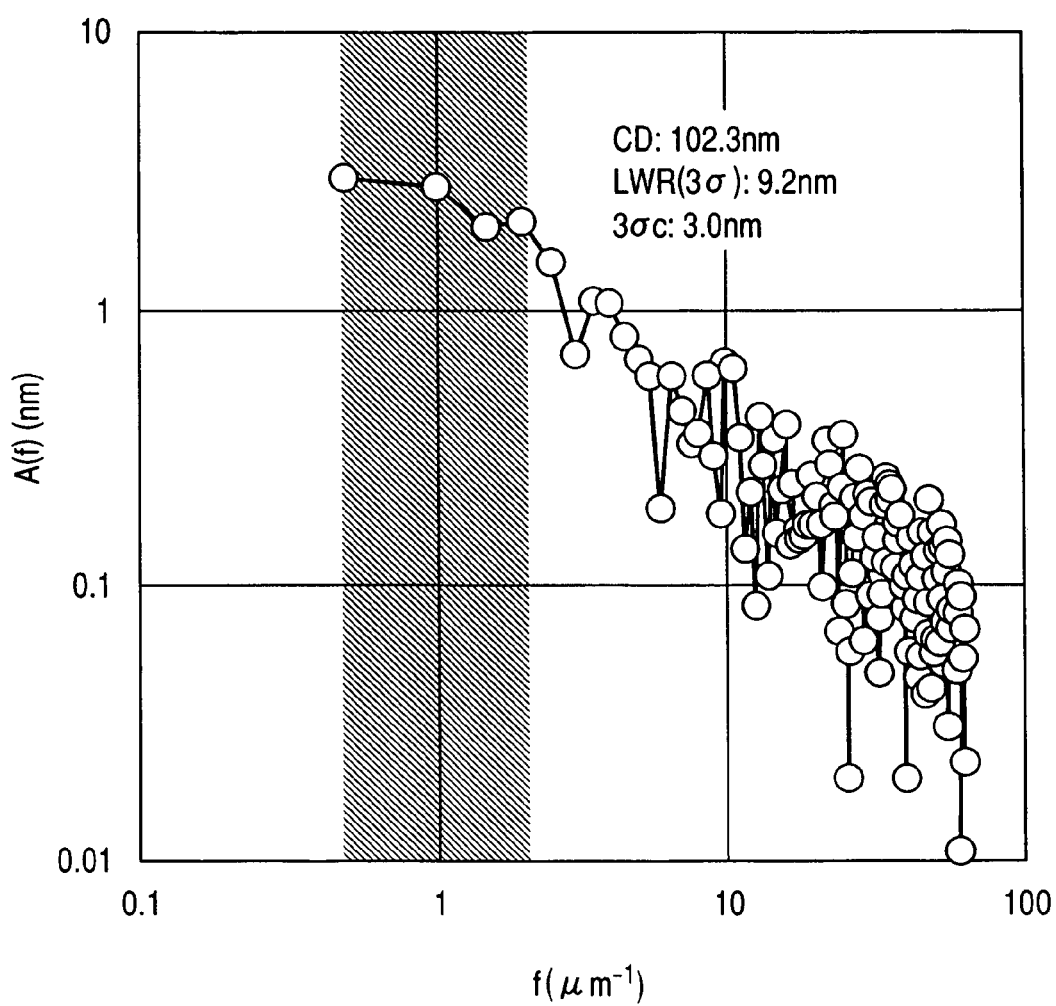
FIG. 9 is a conceptual diagram of display of analysis results obtained in the first embodiment of this invention.

A first embodiment of this invention will be described using FIG. 4 to FIG. 9. FIG. 4 is a schematic diagram showing a structure of inspection equipment used in this embodiment, FIG. 5 is a schematic diagram showing a position of an inspected chip on a wafer in this embodiment, FIG. 6 is a flowchart showing a part of a procedure of analyzing a two-dimensional signal intensity distribution obtained by observation, FIG. 7 is a Fourier spectrum displayed on a display of the inspection equipment, FIG. 8 is a window used for specifying by inputs a region where measurement results of the roughness data are Fourier transformed and absolute values of the Fourier coefficients squared are integrated, and FIG. 9 is a diagram showing an integration region displayed on the spectrum shown in FIG. 7 and a roughness index $3\sigma_c$ obtained from an integration value of the power spectrum $\sigma_c^2$, which are evaluation results displayed on the display of the inspection equipment when analysis of one line pattern is ended.

This embodiment shows an example where inspection using equipment of this invention was performed in an inspection process at the time of semiconductor device production and the yield of manufacture was improved by monitoring the long-period roughness.

In the semiconductor manufacturing process described in this embodiment, the transistor with a structure that is resistant to the short channel effect was produced. Therefore, an influence of line width roughness of a short period was comparatively small. However, performance variation in a transistor by roughness of a long period cannot be disregarded, and might bring a critical yield drop. So, it was necessary to monitor the long-period roughness at the time of dimensional inspection after the end of a lithography process. Any wafer whose index of roughness is equal to or less than a fixed value is put into the next process, but wafers whose indexes of roughness exceed the fixed values go through the lithography again after resist peeling.

Hereafter, a concrete procedure of this embodiment will be presented.

First, a wafer that went through the lithography process was put in the inspection equipment shown in FIG. 4. A wafer 407 is placed on a stage 408 and irradiated with an electron beam 403. The chips on the wafer 501 to be inspected were decided as shown in the shaded portions in FIG. 5. The line pattern 5 μm long and about 100 nm wide existing on the same relative coordinates on this chip is the inspection target pattern. The stage 408 and the irradiating electron beam 403 were moved so that an almost center position of each pattern was set to the center of the field of view, and each pattern was inspected. FIG. 6 shows a procedure of this inspection.

First, a two-dimensional signal intensity distribution of the line pattern was obtained in Step 601. Here it was displayed as a two-dimensional image. In this occasion, magnification in the x-direction (a horizontal direction when facing the image) was 150,000 times and magnification in the y-direction (a direction perpendicular to the x-direction) was 50,000 times. The field of view of the obtained image is 900 nm in the x-direction and 2700 nm in the y-direction. The image was adjusted so that the line pattern was almost parallel to the y-direction. After performing noise reduction processing (Step 602) on this image, an inspection area is set in the central part of the image (Step 603) and the line width was measured (Step 604). The interval of measurement points in the y-direction is 7.8125 nm, the number of measurement points was 256, and the length of the area that was measured (inspection area) in the y-direction was 2000 nm. The roughness data of line widths thus obtained is defined as $w_1, w_2, \ldots, w_{256}$.

Next, in Step 605, these roughness data points were Fourier transformed to yield the absolute values A(f) of the Fourier coefficients. f is the spatial frequency expressed by the following Numerical expression, and its unit was chosen to be μm$^{-1}$.

$$f = \frac{1}{L} \cdot n \quad (n \text{ is an integer.}) \qquad \text{[Numerical expression 7]}$$

L is the length of the inspection area in the y-direction and, in the case of this embodiment, it is 2.0.

Next, the flow proceeded to Step 606, where the Fourier amplitude spectrum and a window for integration-region input were displayed on a display of the inspection equipment. Moreover, on the Fourier amplitude spectrum, the line width average value computed from the Fourier amplitude corresponding to $f_0$ and three times the standard deviation of the line width distribution, namely 3σ, were displayed as CD and LWR, respectively. The former is a value exclusive of variation components of the line width. FIG. 7 and FIG. 8 show these values.

As shown in FIG. 8, a calculation value (in the figure, indicated as Output) and the lower limit and the upper limit of spatial frequency region where the operator intends to perform integration can be set using the window for integration-region input. The calculation value can be selected from among the standard deviation $\sigma_c$ of variation of the data points, two times of it ($2\sigma_c$), three times of it ($3\sigma_c$), six times of it ($6\sigma_c$), and the deviation ($\sigma_c^2$) by mouse operation. The default was $3\sigma_c$. This is because it is general that the degree of line-edge roughness is expressed by three times the standard deviation in the semiconductor manufacture. Moreover, the default value of the lower limit field of the spatial frequency region was set to 0.5. This is because it is desirable to measure roughness in an area whose length is equal to or more than 2 μm along with the line, as mentioned above. Furthermore, the default value of the upper limit field was set to 5. This is based on the background that this invention was made generally for transistors of small gate widths that come with the necessity of measuring the long-period roughness. According to the trend in recent years, small devices, such as memory, have gate widths of about 200 nm. Therefore, corresponding spatial frequency of 5 μm$^{-1}$ was decided as a default value.

Next, the upper limit and the lower limit of the spatial frequency region where the operator intends to perform integration were entered on the window for integration-region input shown in FIG. 8 (Step 607). Here, for the lower limit value, a default value of 0.5 was used, and for the upper limit value, a value of two was entered. These values were decided by the following way of thinking. First, when the value of 0.5 of the former is converted into a spatial period of 2 μm, being equivalent to the length of the inspection area. In order to measure the long-period roughness as correctly as possible, the lower limit of the integration region was set to a value corresponding to this. Regarding the resist material used here, a lot of Fourier amplitude spectra of the line-edge roughness of that pattern have been obtained, and it was confirmed that the parameter $f_0$ became about 2. This production factory is making devices of various gate widths simultaneously. However, dimensional inspection by varying boundary between the long and short periods responsive to the gate width $w_g$ could not be performed. Therefore, a frequency $f_0$ at which f-dependency of A(f) in the spectrum shape changed was defined as a boundary of the long period and short-period roughnesses, and a component whose spatial period was longer than $1/f_0$ was defined as the long-period roughness.

When the integration region was entered, the flow proceeded to Step 608, where a region corresponding to frequencies from f=0.5 to f=2 on the spectrum shown in FIG. 7 is displayed with shading, and at the same time the roughness index $3\sigma_c$ obtained from an integration value $\sigma_c^2$ of the power spectrum was outputted on a screen. FIG. 9 shows this situation. The measurement results were saved in a storage area of the inspection equipment, and inspection of this pattern was ended.

This inspection of the process shown in FIG. 6 was performed to all the line patterns that were intended to be done so on the chip shown in FIG. 5. Next, the quality of the wafer was determined.

In the semiconductor manufacturing process of this embodiment, wafers whose CD values were 95 to 105 nm were determined to be acceptable. This criterion was established because the inspected pattern was the gate pattern of a gate length of 100 nm, and only patterns whose gate lengths fall on a range from 95 to 105 nm should be determined to be acceptable in order to achieve necessary performance (threshold voltage), which was known from a result obtained by simulating the relation between the gate length and the device performance. Moreover, regarding $3\sigma$, 10 nm or less was adopted as the acceptance criterion. This is because it was empirically confirmed that a pattern not satisfying this criterion suffered degradation in the pattern feature and a short circuit occurred in the next process of dry etching. Moreover, regarding the long-period roughness component $3\sigma_c$, 2.5 nm or less was adopted as the acceptance criterion. This is because from a result of simulation ran in advance, it was predicted that in chips not satisfying these criteria, 10% or more of transistors contained therein did not have necessary performance and did not function as devices. If the total 10 patterns of inspected chips all satisfy this criterion, the wafer is determined to be acceptable and put into the next process. This is because as a guidance of achieving a yield of 90% or more, it was necessary for the all the ten chips selected in a wafer to be acceptable. Since this wafer does not satisfy the criteria of the acceptable in the above-mentioned chip, this wafer was put into the lithography process again.

Thus, since execution of this invention made it possible to remove such a wafer as having a high possibility of being determined to be unacceptable in the early stage and repeat the manufacture, the yield was improved and the number of waste wafers decreased largely, reducing an environmental load.

Moreover, CD values acquired in the above-mentioned procedure are hardly affected by line-edge roughness. Therefore, when computing CD uniformity across a wafer plane and CD variation among wafers, the use of these values enables the amounts of these values to be computed more accurately.

Incidentally, it is also possible to execute the above-mentioned procedure automatically without the operator. In that case, entry of the integration region has been made in advance, and there is no need to enter numerical values in FIG. 8 for each inspection pattern. Moreover, the inspection results obtained for each chip are put in a file and saved automatically.

Note that in the above-mentioned procedure, the spectrum displayed on the display was chosen to be Fourier amplitude spectrum, but a power spectrum may be used. Calculation actually done is the integration on the power spectrum. Displaying the power spectrum brings a merit that it is easy for the operator to understand intuitively and that the display helps the operator notice improper operations.

Second Embodiment

Figure 10:
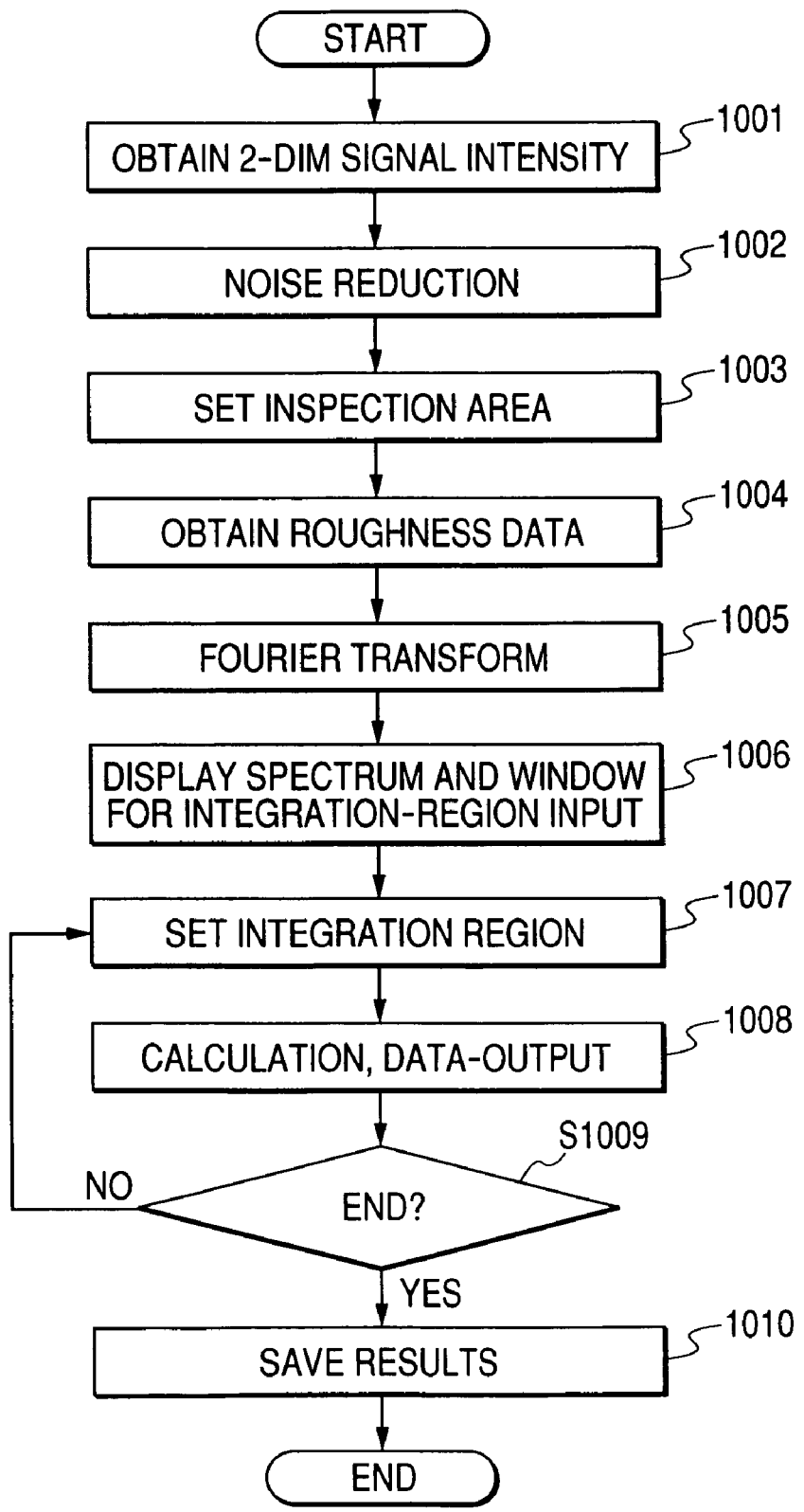
FIG. 10 is a flowchart showing a part of procedure in the second embodiment of this invention.

A second embodiment of this invention will be described using FIG. 4 and FIG. 10. FIG. 4 is a schematic diagram showing a structure of the inspection equipment that was used in this embodiment. FIG. 10 is a flowchart showing a part of procedure for analyzing a two-dimensional signal intensity distribution obtained in this embodiment as a result of observation.

This embodiment shows an example where inspection that uses the equipment of this invention is performed in an inspection process at the time of semiconductor device production, and the yield of manufacture is improved by monitoring the short-period roughness besides the long-period roughness.

In the semiconductor manufacturing process described in this embodiment, transistors of gate widths $w_g$ of about 300 nm were mainly made, and there was a possibility that performance variation in a transistor by the roughness whose spatial period is longer than 300 nm might cause a yield drop. At the same time, there was found out a phenomenon that if small roughness whose spatial period was equal to or less than 100 nm existed on the resist pattern, the part was damaged in dry etching and scraped off. For this reason, at the time of dimensional inspection after the end of the lithography process, there arose a need to monitor the short-period roughness whose spatial period was equal to or less than 100 nm as well as the long-period roughness whose spatial period was equal to or more than 300 nm.

Hereafter, a concrete procedure of this embodiment will be presented. Incidentally, all of used inspection equipment, chip placement on a wafer, and an inspection target pattern are the same as those in the first embodiment.

Similarly with the first embodiment, first, a wafer having gone through the lithography process was put in the inspection equipment shown in FIG. 4. An inspected pattern and its position were the same as those in the first embodiment.

Contents of inspection performed to each pattern will be described using FIG. 10.

First, in Step 1001, an electron microscope observation image of the line pattern was obtained. Observation magnification and the size of the field of view were the same as values in Step 601 of the first embodiment. Noise reduction processing (Step 1002) was performed on this image, and the inspection area was set up appropriately (Step 1003). Next, roughness data of line widths was acquired, as shown in Step 1004. Conditions in this case were the same as those in Step 604 of the first embodiment. Next, the flow proceeded to Step 1005, where the roughness data is Fourier transformed, and in Step 1006, its spectrum was displayed. At the same time, the window for integration-region input was displayed.

Next, on the displayed window for integration-region input, a lower limit and an upper limit of the integration spatial frequency region were entered (Step 1007). Here, first, they were set to 0.5 and 3.3, respectively, as a calculation region of the index of long-period roughness.

These values were decided by the following way of thinking. First, a value of 0.5 of the former is 2 μm in terms of spatial period, corresponding to the length of an inspection area. According to previous research, if roughness is measured up to a spatial period of about 2 μm, its rough tendency can be grasped. Then, the inspection area length was set to 2 μm and the lower limit of the integration region was also set to a value corresponding to this. Moreover, since transistors of gate widths of 300 nm were mainly made on the wafer, a component whose spatial period is longer than this value was intended to be observed. A value of 3.3 is a spatial frequency corresponding to a spatial period of 300 nm.

When the integration region was entered, the flow proceeded to Step 1008, where an integration value $\sigma_c^2$ of the power spectrum of a region corresponding to frequencies from f=0.5 to f=3.3 was calculated, and the roughness index $3\sigma_c$ obtained from this value was outputted.

Next, since the index of short-period roughness was also intended to be obtained, the flow did not end in Step 1008 (selecting N in Step 1009), but proceeded to Step 1007. Other values were entered on the window for integration-region input. The entered lower limit was 10 and the entered upper limit was 100. This lower limit value is a frequency corresponding to the maximum period (100 nm) that is considered to cause a large effect on the pattern after dry etching. Moreover, since components whose spatial periods were shorter than 10 nm were filtered by noise reduction, the upper limit of the integration region was set to a frequency to which this value corresponded.

When these numerical values were entered, the flow proceeded to Step 1008, where the index of short-period roughness was outputted. Since the inspection for this pattern ended by this, the flow proceeded to Step 1010, where all the evaluation results described above were saved in the storage area of the inspection equipment, and the inspection of this pattern was ended.

This inspection was performed to all the line patterns that were intended to be done so on the chip shown in FIG. 5. Next, the quality of the wafer was estimated.

In a semiconductor manufacturing process of this embodiment, acceptance criteria were: CD value was from 95 to 105 nm; 3σ was 10 nm or less; the long-period roughness $3\sigma_c$ was 5 nm or less; and the short-period roughness $3\sigma_c$ was 2.5 nm or less. If total 10 patterns of the chips inspected in a wafer all satisfy these acceptance criteria, the wafer was determined to be acceptable and was put into the next step. Since all the chips in this wafer satisfied these criteria, this wafer was put into the next step, dry etching.

Thus, since execution of this invention makes it possible to remove such a wafer as has high possibility of becoming a defective in its early stage and repeat the manufacture, the yield is improved and the number of waste wafers decreased largely, reducing an environmental load.

Third Embodiment

A third embodiment of this invention will be described using FIG. 6, FIG. 11, and FIG. 12. FIG. 6 is a flowchart showing a part of a procedure of analyzing an electron microscope observation image in this embodiment, FIG. 11 shows a patter under a resist film 1101 of a sample 1102 inspected in this embodiment, and FIG. 12 is an example of a resist pattern inspected in this embodiment.

This embodiment shows an example where inspection using the equipment of this invention is performed in an inspection process at the time of semiconductor device production and a variation in a line width that has a specific frequency is monitored, whereby the yield of manufacture is improved.

Figure 11:
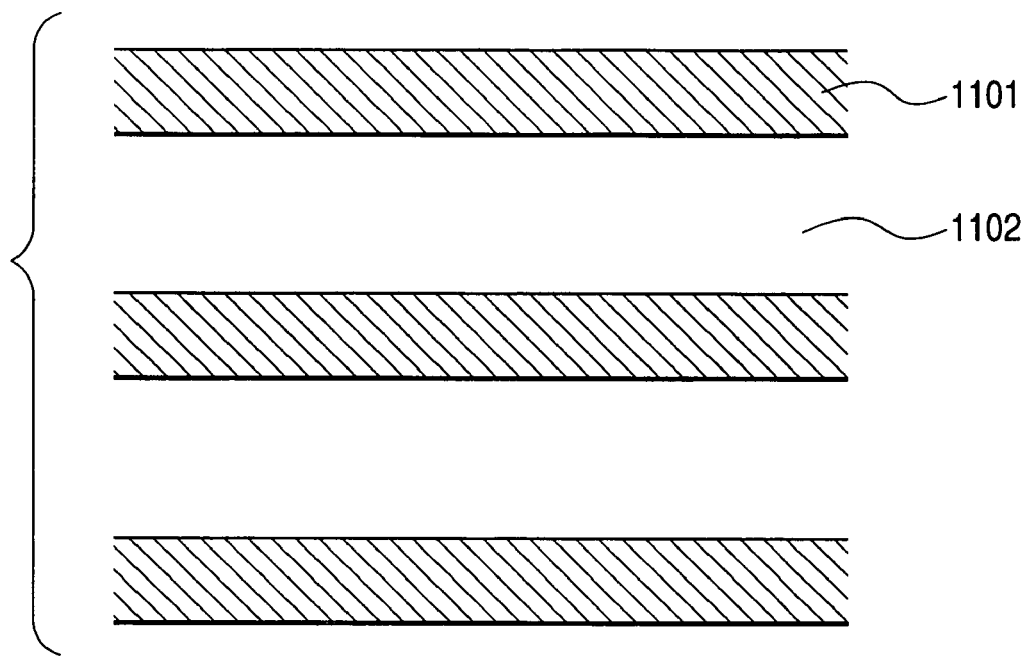
FIG. 11 is a conceptual diagram of a line pattern of a metal material formed under a resist film that is analyzed in the third embodiment of this invention.

In the semiconductor manufacturing process described in this embodiment, prior to steps in which a layer of important line pattern is processed, a line pattern of a metal material running in a direction perpendicular to a line for gate was formed as shown in FIG. 11. An insulating material is deposited on this metal pattern and processed to be flat. Subsequently an anti-reflective layer is formed, a resist film is deposited by spin-coating, and this resist film is processed into the form of a line.

Figure 12:
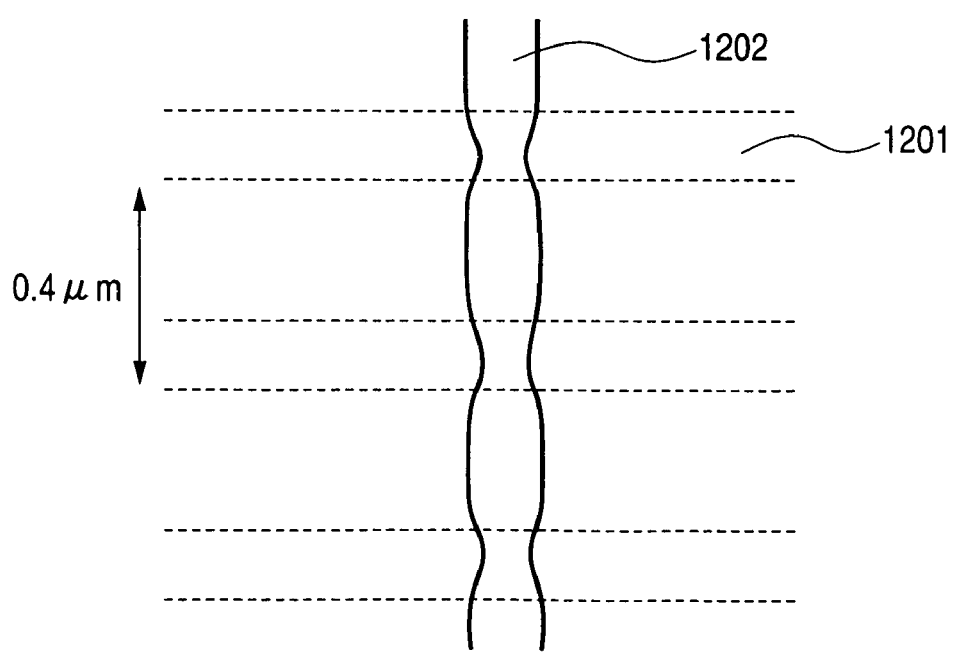
FIG. 12 is a conceptual diagram of a resist pattern that is analyzed in the third embodiment of this invention and a line pattern of a metal material formed under its layer.

However, if thickness of anti-reflective layer is not proper, reflection from the metal pattern of the underlayer affects the resist pattern and the line width may be varied as shown in FIG. 12. Numeral 1201 in the figure is a line pattern of a metal existing under the anti-reflective layer, and the resist pattern 1202 is thinned in a portion above the metal. Because of this, there arose a need to monitor components of line width variation that synchronized with a spatial period of the metal pattern underlying the resist at the time of dimensional inspection after the end of the lithography process. Incidentally, in an image of the metal pattern of this embodiment, a pitch in the y-direction was 0.4 μm.

Hereafter, a concrete procedure of this embodiment will be presented.

In this inspection, each pattern described in the first embodiment was inspected. The procedure is expressed in FIG. 6 as with the first embodiment. The field of view was moved on the inspection target pattern, and a two-dimensional signal intensity distribution was acquired in Step 601. Observation magnification and a size of the field of view were the same as those in the first embodiment.

Next, the flow proceeded to Step 602, when noises were reduced, and subsequently the inspection area was set in Step 603. Next, roughness data of line widths was acquired in Step 604. Also here, the measurement parameters were the same as those in the first embodiment. Next, the result of performing the Fourier transform in Step 605 was displayed on an inspection equipment monitor along with the window for integration-region input in Step 606.

Here (in Step 607), a lower limit of 2 and an upper limit of 3 were entered for the integration region, and the component $3\sigma_c$ was extracted. This component $3\sigma_c$ was 4.7 nm, whereas a roughness index of the whole region ($3\sigma$) was 10.2 nm. These numerical values were saved in the storage area of the inspection equipment.

The above-mentioned value indicates that a variation in the line width of a frequency corresponding to pitch 0.4 μm is very large. In this embodiment, when a ratio of $3\sigma_c$ computed in the above-mentioned integration region to a roughness index of $3\sigma$ of the whole region became a value of 0.4 or more, it was determined that thickness of the antireflective layer was not proper. Therefore, it was concluded that thickness of antireflective layer is not proper.

By this invention, it was possible to monitor a variation in the line width resulting from a specific cause. Moreover, based on this result, a film forming process of the anti-reflective layer was inspected. The inspection showed that a deadline of the material of the anti-reflective layer was expired, which caused occurrence of nonuniformity in its viscosity. Thus, it becomes possible to specify the cause of roughness occurrence and undertake remedial measures.

Fourth Embodiment

Figure 13:
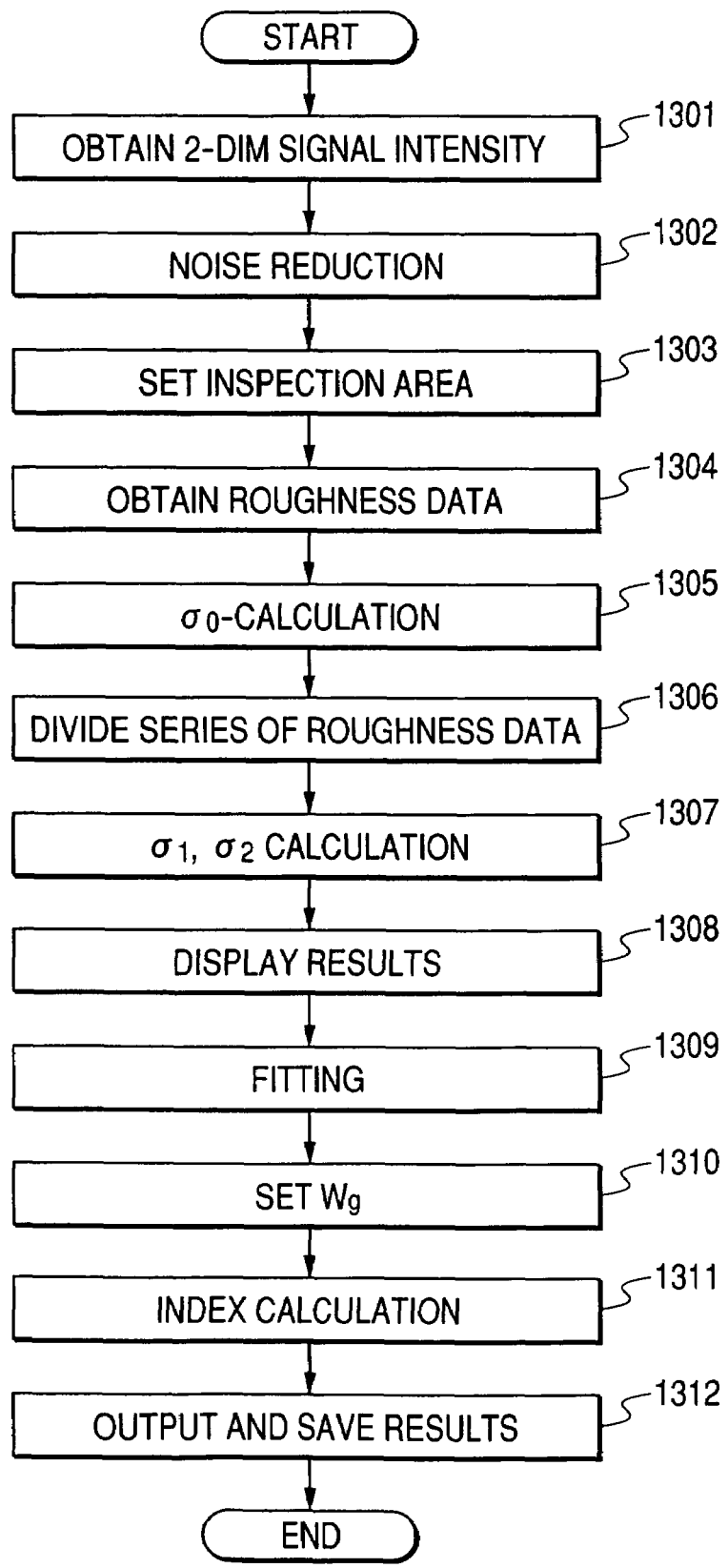
FIG. 13 is a flowchart showing a part of procedure in the fourth embodiment of this invention.
Figure 14:
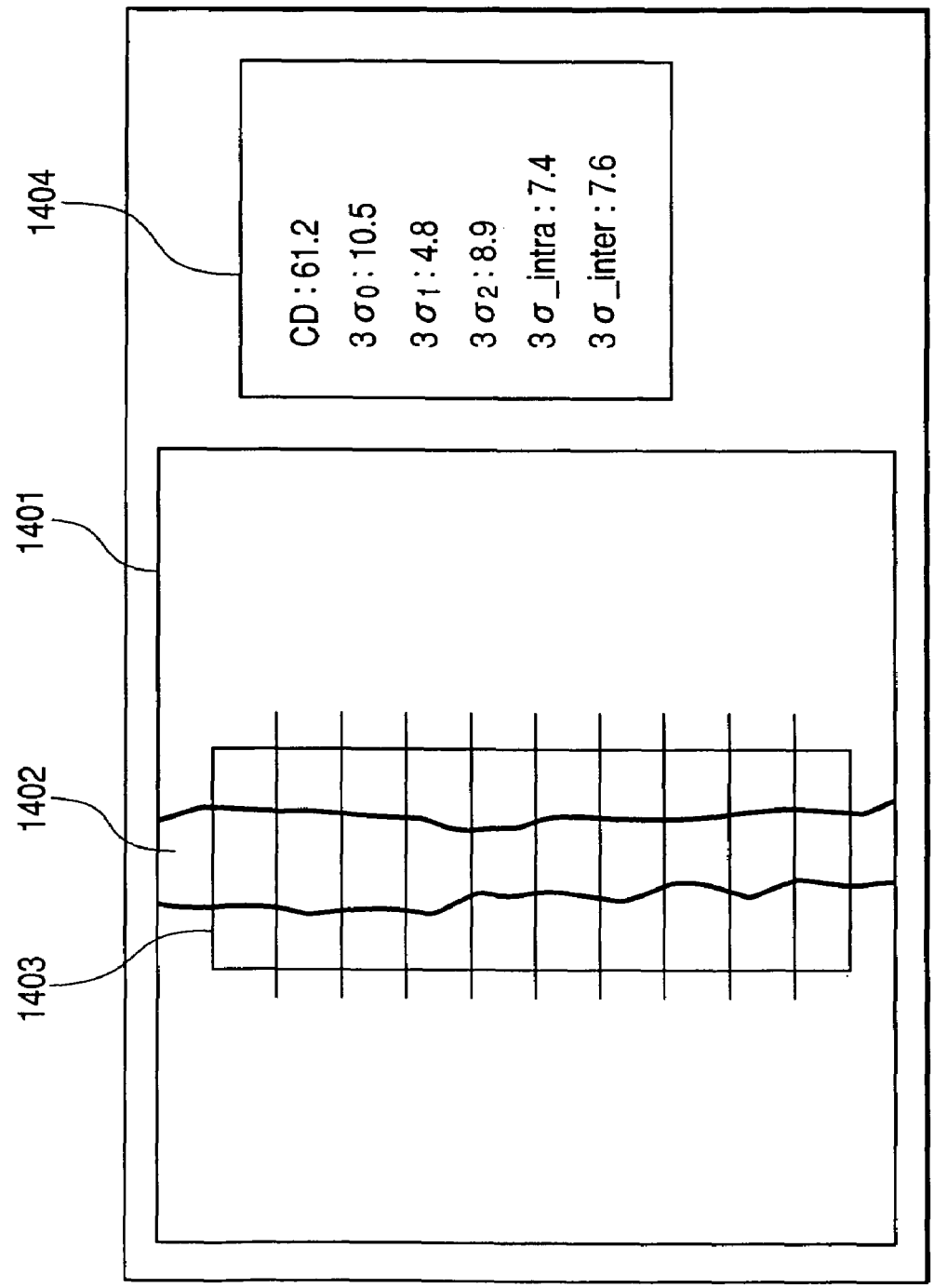
FIG. 14 is a conceptual diagram of display of analysis results obtained in the fourth embodiment of this invention.

A fourth embodiment of this invention will be described using FIG. 4, FIG. 5, FIG. 13, and FIG. 14. FIG. 4 is a schematic diagram showing a configuration of the inspection apparatus 401 in this embodiment; FIG. 11 a schematic diagram showing a position on a chip that is inspected in this embodiment; FIG. 13 is a flowchart showing a part of a procedure of analyzing a two-dimensional signal intensity distribution obtained by observation in this embodiment; and FIG. 14 is an outline diagram of a window displayed on the screen as a result of the analysis in this embodiment.

This embodiment shows an example where the inspection using the equipment of this invention is performed in the inspection process at the time of semiconductor device production, and the yield of manufacture is improved by monitoring both the short-period roughness causing performance degradation and the long-period roughness causing performance variation of the transistor of a gate width to which attention is paid.

In the semiconductor manufacturing process described in this embodiment, transistors of gate widths $w_g$ of about 500 nm were mainly made, and there was a possibility that performance variation in a transistor caused by the roughness whose spatial period is longer than 500 nm might cause a yield drop. At the same time, it was also necessary to evaluate rapidly the roughness in the transistor area that is related to performance degradation of a transistor. For this reason, there arose a need to monitor the long-period roughness and the short-period roughness without increasing inspection time at the time of dimensional inspection after the end of the lithography process.

A concrete procedure is shown below. First, a wafer after completing the lithography process was put in the inspection equipment shown in FIG. 4. The wafer 407 was placed on the stage 408 and irradiated with the electron beam 403. The chips on the wafer to be inspected were specified as shown in shaded portions in FIG. 5. The line pattern that exists on the same relative coordinates and has a length of 3 μm and a width of about 60 nm on each chip is the inspection target pattern. The stage 408 and the irradiation electron beam 403 were moved so that almost center position of each pattern is set to the center of the field of view, and each pattern was inspected by software of the inspection equipment. A procedure of this inspection is shown in FIG. 13.

First, a two-dimensional signal intensity distribution of the line pattern was obtained in Step 1301. Here, this was displayed as a two-dimensional image. In this occasion, magnification is 200,000 times in an x-direction (a horizontal direction facing the image) and 60,000 times in a y-direction (a perpendicular direction to the x-direction); the field of view of the obtained image measures 675 nm in the x-direction and 2250 nm in the y-direction. The image was adjusted so that the line pattern was almost parallel to the y-direction. After noise reduction processing on this image (Step 1302), an inspection area was set in the central part of the image (Step 1303). Then, measurement was done automatically and the roughness data was acquired (Step 1304). The interval of the measurement point in the y-direction was 10 nm and the number of measurement points was 200. The length of the area where measurement was done in the y-direction was 2000 nm. The roughness data of the line widths obtained in this way are defined as $w_1, w_2, \ldots, w_{200}$. Next, in Step 1305, the standard deviation $\sigma_0$ of these 200 data was calculated. This value was 3.5 nm.

Next, the flow proceeded to Step 1306. Here, 200 data points were divided into a total of 10 groups each of which consisted of 20 data points. The 20 data points must be consecutive. That is, the data points contained in the first group were w1, w2, . . . , w20; the data points contained in the second group were w21, w22, . . . , w40; and the data points contained in the tenth group were w181, w182, . . . , w200. Each of the groups newly created here constitutes roughness data of line widths of an area corresponding to a length of 200 nm. Next, the flow proceeded to Step 1307, where the average and the standard deviation of the 20 data points in each group were computed for the ten groups obtained in the previous step. For these data points, the standard deviations are defined as σ1,1, σ1,2, . . . , σ1,10, and the averages are defined as CD1, CD2,CD10. Further, the average σ1 of the 10 standard deviations and the standard deviation σ2 of the 10 averages were calculated. In the next Step 1308, the calculation results were outputted on an observation image display window. In this manufacturing process, since conventionally a value of three times the standard deviation was used as a criterion rather than the standard deviation, values of 3σ0, 3σ1, and 3σ2 were outputted.

Next the flow proceeded to Step 1309, where for three set of values $(L_1, \sigma_0)$, $(L_2, \sigma_1)$, and $(L_2, \sigma_2)$ functions shown in (Numerical expressions 4) were fitted using theoretical curves g(L) and h(L). Here, $L_1$=200 nm and $L_2$=2000 nm. A set of the theoretical curves g(L) and (L) was saved in advance in the storage area of the inspection equipment. These theoretical curves were calculated by simulation.

After values of fitting parameters were determined, the flow proceeded to Step 1310, where the gate width of a translator to which attention was paid or a length wg that the operator intended to define as a boundary 1402, 1403 in display window 1401 (FIG. 14) of the long and short periods was set. Here, it was set to 500 nm. Next, in Step 1311, values 1404 of an index of the short-period roughness 3σ_intra (wg) and an index of the long-period roughness 3σ_inter (wg) were calculated to be 7.4 nm and 7.6 nm from (Numerical expression 6), respectively, and the results are output and saved (Step 1312). FIG. 14 shows this situation.

This inspection was performed to all the line patterns that were intended to be done so on the chip shown in FIG. 5. Next, the quality of the wafer was determined. In the semiconductor manufacturing process of this embodiment, the criteria were as follows: CD value was 55 to 65 nm; 3σ was 12 nm or less; the index of short-period roughness 3σ_intra ($w_g$) was 9 nm or less; the index of long-period roughness 3σ_inter ($w_g$) was 8 nm or less. If total 10 patterns of the chips that were inspected all satisfy the criteria, the wafer was determined to be acceptable, and was put into the next process. Since all the chips in this wafer satisfied these criteria, this wafer was put into the next process, dry etching.

Incidentally in the above-mentioned example, a value of $w_g$ was entered in each inspection, but it was possible to eliminate a step of entering the value of $w_g$ by setting this value in advance. In this case, the inspection time is shortened.

Moreover, by using the above-mentioned indexes of short-period and long-period roughnesses, it is possible to estimate performance degradation in a transistor and its variation, for example, by means of techniques described in Non-patent document 1 and Non-patent document 7. Concretely, from the result of 3σ_intra, assuming that an internal gate length distribution of transistors is a Gaussian distribution with a center value equal to a design value and the variance equal to σ_intra$^2$, a fall of threshold voltage and an increase in dark current can be calculated. Moreover, from the result of 3σ_inter, assuming that the internal gate length distribution described above becomes a Gaussian distribution with the center value of the gate length distribution described above having a width of about σ_inter, a distribution of threshold voltages in the case where a plurality of transistors exist can be calculated.

Fifth Embodiment

Figure 15:
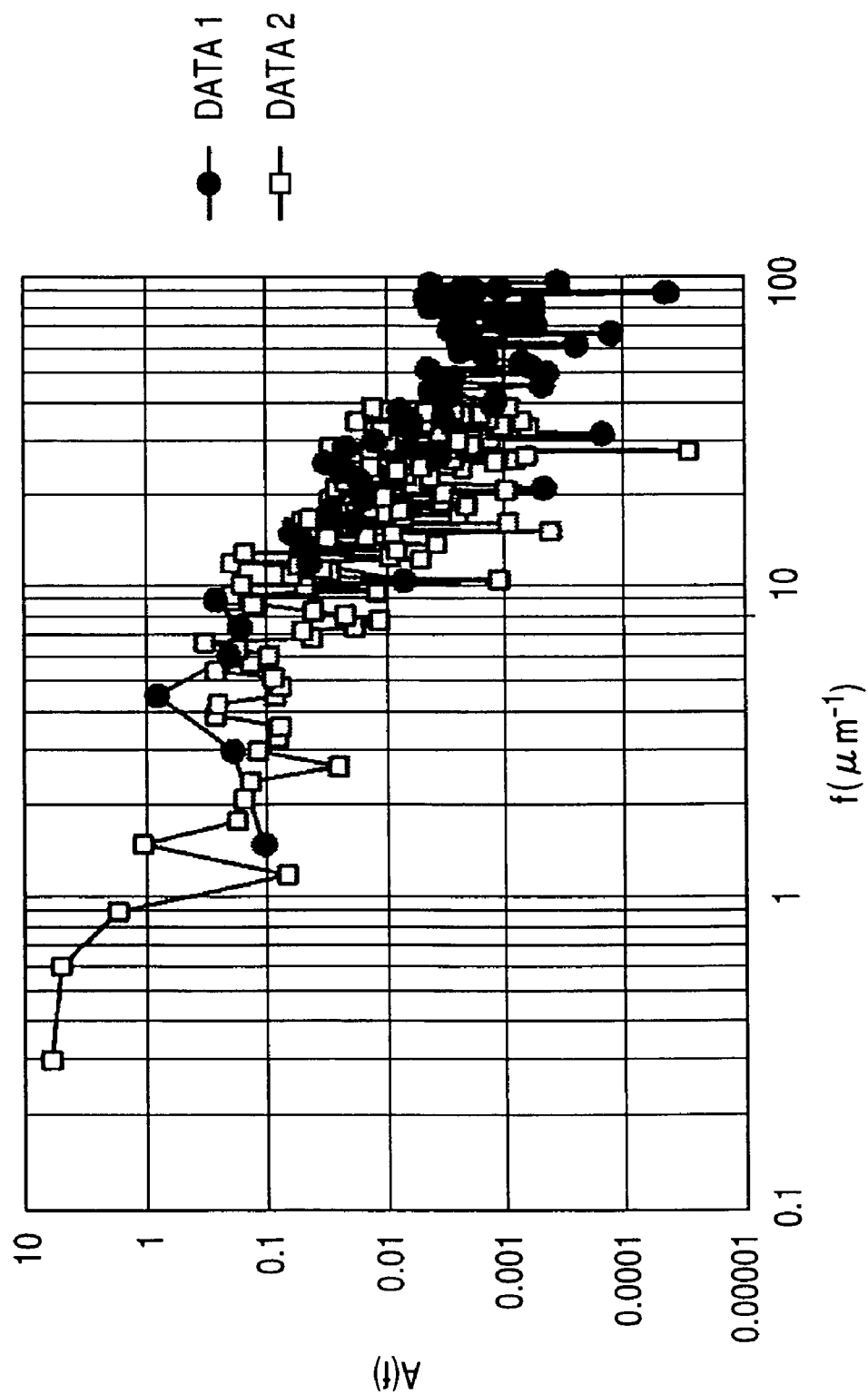
FIG. 15 is a power spectrum obtained in the fifth embodiment of this invention.

A fifth embodiment of this invention will be described using FIG. 15. FIG. 15 is a schematic diagram of a power spectrum obtained in this embodiment.

This embodiment shows an example where this invention is applied to two pattern images having different observation conditions and the magnitude of roughness is determined in a research and development phase for constructing a semiconductor device production process.

In this embodiment, the equipment used in the embodiment 1 was used. When this embodiment was executed, no wafer sample was loaded in the equipment, and the equipment was used in order to analyze two images saved in the storage area inside the computer. The pattern shown in these two observation images was a line pattern of one line and was almost in the center of the image.

First, a first observation result was called up from the storage area and displayed on the screen. Observation magnification of this image was 150,000 both in the x-direction and the y-direction. The length and width of the area displayed in the image were both 900 nm. The image consisted of 512 pixels both in vertical and horizontal directions, and it was necessary to measure the line width etc. at a position corresponding to the pixel. As a result of noise reduction processing on the image, substantial resolution in the y-direction became 5.3 nm. 128 points of local line widths of the line pattern within this image were measured at intervals of 5.3 nm and a first roughness data was obtained. It has no meaning to set measurement interval to smaller than substantial resolution (here 5.3). However, since it is preferable to measure as high a frequency component as possible, it was set equal to substantial resolution. Second, a reason why roughness data was specified to have 128 terms was that it was necessary to set the number to any numerical value of powers of 2 in order to perform fast Fourier transform, and that the number was set to as large a value as possible within a range in which a product of the number and the measurement interval did not exceed 900 nm. This set of roughness data is equivalent to a length of 675 nm on the line. These data were Fourier transformed and the power spectrum was displayed.

Next, the second observation result was called up from the storage area and displayed. The observation magnifications of this image were 150,000 times in the x-direction and 40,000 times in the y-direction. The height and width of the area displayed in the image were 3375 nm and 900 nm, respectively. As a result of noise reduction processing on the image, the substantial resolution in the y-direction became 13.2 nm. 128 points of local line widths of the line pattern within this image were measured at intervals of 13.2 nm and a second set of roughness data points was obtained. How to choose these values is the same as that in the case of the first image. This data is equivalent to the length of 1687.5 nm on the line. A power spectrum of this set of roughness data points was also displayed on the same graph as the power spectrum of the first roughness data points. FIG. 15 shows this situation.

For a value of integration region, it is recommended to use a frequency region common to the first and second spectra may be used. This can be easily determined by seeing a power spectrum. Here, the integration region was set to 2 μm$^{-1}$ to 30 μm$^{-1}$, these values were entered in the window for integration-region input of each set of data points. 3σ$_c$=4.2 nm for the first roughness data points and 6.3 nm for the second roughness data points were obtained, and it was found that the pattern of the first image had smaller roughness.

Calculating the integral value 3σ$_c$ with the integration range being set is equal to deciding the sampling conditions (whole length and sampling interval) of roughness data, calculating the roughness data, and finding 3σ from the data. However, without this function, it is impossible to sample under the same conditions two images observed under different conditions because of complexity of the procedure. This invention makes it possible to decide an integration region with an easy procedure and compare two data.

The evaluation method of fine pattern feature and its equipment according to this invention evaluates frequency components that cause important effects on device performance among frequency components of the line-edge roughness. This evaluation enables pattern feature inspection that suits a devise structure and final specifications of a device, thereby improving device productivity.

What is claimed is:

1. An evaluation method of a semiconductor device, comprising the steps of;
   scanning a semiconductor device including a pattern with an electron beam irradiating thereon, detecting secondary electrons emitted from the semiconductor device or reflected electrons, and acquiring an information of a two-dimensional distribution of an intensity of the electrons;
   measuring positions of points constituting a boundary of the pattern at a constant interval of 10 nm or less along a longitudinal direction and at 2 µm or more along the longitudinal direction to generate roughness data of the pattern;

discrete Fourier transforming the roughness data; and adding the square values of the absolute values of Fourier coefficients, acquired by the discrete Fourier transformation, within a predetermined range of frequency thereon, outputting an index representing characteristics of the pattern features, wherein the index is at least one or more values selected from among the total value of the square values, a square root of the total value, two times the square root of the total value, three times the square root of the total value, and six times the square root of the total value.

2. An evaluation method of a semiconductor device, comprising the steps of:

scanning a semiconductor device including a pattern with an electron beam irradiating thereon, detecting secondary electrons emitted from the semiconductor device or reflected electrons, and acquiring an information of a two-dimensional distribution of an intensity of the electrons;

measuring positions of points constituting a boundary of the pattern at a constant interval of 10 nm or less along a longitudinal direction and at 2 µm or more along the longitudinal direction to generate roughness data of the pattern;

discrete Fourier transforming the roughness data; and adding the square values of the absolute values of Fourier coefficients, acquired by the discrete Fourier transformation, within a predetermined range of frequency thereon, outputting an index representing characteristics of the pattern feature, wherein an upper limit or lower limit of the predetermined range of frequency is specified by inputs or set up in advance and is an inverse of a gate width of a transistor that is made.

3. A fabrication method of a semiconductor device including a step of inspecting a semiconductor wafer on which a pattern is formed, comprising the steps of:

detecting secondary electrons emitted from the semiconductor device or reflected electrons by scanning a semiconductor wafer including a pattern with an electron beam irradiating thereon, acquiring an information of a two-dimensional distribution of an intensity of the electrons, measuring positions of points constituting a boundary of the pattern at a constant interval of 10 nm or less along a longitudinal direction and at 2 µm or more along the longitudinal direction to generate roughness data of the pattern;

calculating a critical dimension value and deviation of the data;

discrete Fourier transforming the roughness data;

adding the square values of the absolute values of Fourier coefficients, acquired by the discrete Fourier transformation, within a predetermined range of frequency thereon, outputting an index representing characteristics of the pattern feature; and deciding to pass or fail the semiconductor wafer if the critical dimension value, the deviation and the index meet the requirement of the standard values specified in advance, and displaying a diagram in which absolute values of Fourier coefficients obtained by Fourier transforming the roughness data or squares of absolute value of Fourier coefficients are plotted versus the frequency, wherein if the critical dimension value, the deviation and the index meet the requirement, the wafer is transferred to a next semiconductor fabrication process, and wherein if the critical dimension value, the deviation and the index do not meet the requirement, the wafer is transferred to a reformation process of the pattern of the wafer.

4. The evaluation method of the semiconductor device, according to claim 3, further comprising the step of displaying above the diagram a specific frequency region that the operator specified by inputs.

5. An evaluation method of a semiconductor device, comprising the steps of:

scanning a semiconductor device including a pattern with an electron beam irradiating thereon, detecting secondary electrons emitted from the semiconductor device or reflected electrons, and acquiring an information of a two-dimensional distribution of an intensity of the electrons;

measuring positions of points constituting a boundary of the pattern at a constant interval of 10 nm or less along a longitudinal direction and at 2 µm or more along the longitudinal direction to generate roughness data of the pattern;

discrete Fourier transforming the roughness data;

adding the square values of the absolute values of Fourier coefficients, acquired by the discrete Fourier transformation, within a predetermined range of frequency thereon, outputting an index representing characteristics of the pattern feature; and calculating a square of an absolute value of the Fourier series that is obtained by Fourier transforming the roughness data of the pattern edges or the roughness data of pattern dimensions, namely a power spectrum $P(f)$, as an index representing characteristics of the evaluation target pattern feature and presenting a menu so that the operator can select any of a $\sigma c\ 2$ that is a total of all the $P(f)$ that satisfy a specific integration region of the spatial frequency f (from a µm−1 to b µm−1), $\sigma c$, $2\sigma c$, $3\sigma c$ and $6\sigma c$ to urge the operator to selection.

6. A fabrication method of a semiconductor device including a step of inspecting a semiconductor wafer on which a pattern is formed, comprising the steps of:

detecting secondary electrons emitted from the semiconductor device or reflected electrons by scanning a semiconductor wafer including a pattern with an electron beam irradiating thereon, acquiring an information of a two-dimensional distribution of an intensity of the electrons, measuring positions of points constituting a boundary of the pattern at a constant interval of 10 nm or less along a longitudinal direction and at 2 µm or more along the longitudinal direction to generate roughness data of the pattern;

calculating a critical dimension value and deviation of the data;

discrete Fourier transforming the roughness data;

adding the square values of the absolute values of Fourier coefficients, acquired by the discrete Fourier transformation, within a predetermined range of frequency thereon, outputting an index representing characteristics of the pattern feature; and deciding to pass or fail the semiconductor wafer if the critical dimension value, the deviation and the index meet the requirement of the standard values specified in advance, wherein if the critical dimension value, the deviation and the index meet the requirement, the wafer is transferred to a next semiconductor fabrication process, and wherein if the critical dimension value, the deviation and the index don't meet the requirement, the wafer is transferred to a reformation process of the pattern of the wafer, and wherein an upper limit or lower limit of the predetermined range of frequency is specified by inputs or set up in advance and is an inverse of a gate width of a transistor that is made.

7. An evaluation method of a semiconductor device, comprising the steps of:

detecting secondary electrons emitted from the semiconductor device or reflected electrons by scanning a semiconductor wafer including a pattern with an electron beam irradiating thereon, acquiring an information of a two-dimensional distribution of an intensity of the electrons, measuring positions of points constituting a boundary of the pattern at a constant interval of 10 nm or less along a longitudinal direction and at 2 μm or more along the longitudinal direction to generate roughness data of the pattern;

calculating a critical dimension value and deviation of the data;

discrete Fourier transforming the roughness data;

adding the square values of the absolute values of Fourier coefficients, acquired by the discrete Fourier transformation, within a predetermined range of frequency thereon, outputting an index representing characteristics of the pattern feature;

deciding to pass or fail the semiconductor wafer if the critical dimension value. the deviation and the index meet the requirement of the standard values specified in advance; and displaying a diagram in which absolute values of Fourier coefficients obtained by Fourier transforming the roughness data or squares of absolute value of Fourier coefficients are plotted versus the frequency, wherein if the critical dimension value, the deviation and the index meet the requirement, the wafer is transferred to a next semiconductor fabrication process, and wherein if the critical dimension value, the deviation and the index do not meet the requirement, the wafer is transferred to a reformation process of the pattern of the wafer.

8. The fabrication method of the semiconductor device, according to claim 7, further comprising the step of:

displaying above the diagram a specific frequency region that the operator specified by inputs.

9. An evaluation method of a semiconductor device, comprising the steps of:

detecting secondary electrons emitted from the semiconductor device or reflected electrons by scanning a semiconductor wafer including a pattern with an electron beam irradiating thereon, acquiring an information of a two-dimensional distribution of an intensity of the electrons;

measuring positions of points constituting a boundary of the pattern at a constant interval of 10 nm or less along a longitudinal direction and at 2 μm or more along the longitudinal direction to generate roughness data of the pattern;

calculating a critical dimension value and deviation of the data;

discrete Fourier transforming the roughness data;

adding the square values of the absolute values of Fourier coefficients, acquired by the discrete Fourier transformation, within a predetermined range of frequency thereon, outputting an index representing characteristics of the pattern feature;

deciding to pass or fail the semiconductor wafer if the critical dimension value, the deviation and the index meet the requirement of the standard values specified in advance; and calculating a square of an absolute value of the Fourier series that is obtained by Fourier transforming the roughness data of the pattern edges or the roughness data of pattern dimensions, namely a power spectrum P (f), as an index representing characteristics of the evaluation target pattern feature and presenting a menu so that the operator can select any of σ c2 that is a total of all the P (f) that satisfy a specific integration region of the spatial frequency f (from a μm−1 to b μm−1), σ c, 2 σ c, 3 σ c and 6 σ c to urge the operator to make a selections, wherein if the critical dimension value, the deviation and the index meet the requirement, the wafer is transferred to a next semiconductor fabrication process, and wherein if the critical dimension value, the deviation and the index do not meet the requirement, the wafer is transferred to a reformation process of the pattern of the wafer.

* * * * *

UNITED STATES PATENT AND TRADEMARK OFFICE
CERTIFICATE OF CORRECTION

| | | |
|---|---|---|
| PATENT NO. | : 7,684,937 B2 | Page 1 of 1 |
| APPLICATION NO. | : 12/078840 | |
| DATED | : March 23, 2010 | |
| INVENTOR(S) | : Yamaguchi et al. | |

It is certified that error appears in the above-identified patent and that said Letters Patent is hereby corrected as shown below:

On the Title Pg, Under Item (73) please delete:

"Hitachi, Ltd."

and insert:

-- Hitachi High-Technologies Corporation --

Signed and Sealed this

Twenty-fifth Day of May, 2010

David J. Kappos
*Director of the United States Patent and Trademark Office*